US012564671B2

(12) United States Patent
Govari et al.

(10) Patent No.: US 12,564,671 B2
(45) Date of Patent: Mar. 3, 2026

(54) PHACOEMULSIFICATION IRRIGATION APPARATUS WITH LOAD CELL AND OPTICAL SENSOR

(71) Applicant: JOHNSON & JOHNSON SURGICAL VISION, INC., Irvine, CA (US)

(72) Inventors: Assaf Govari, Haifa (IL); Christopher Thomas Beeckler, Brea, CA (US); Vadim Gliner, Haifa (IL); Amit Fuchs, Hogla (IL); Ilya Sitnitsky, Nahariya (IL); Eran Aharon, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 932 days.

(21) Appl. No.: 17/749,421

(22) Filed: May 20, 2022

(65) Prior Publication Data

US 2023/0039864 A1 Feb. 9, 2023

Related U.S. Application Data

(60) Provisional application No. 63/230,741, filed on Aug. 7, 2021.

(51) Int. Cl.
*A61M 3/02* (2006.01)
*B06B 1/02* (2006.01)
(Continued)

(52) U.S. Cl.
CPC ........ *A61M 3/0275* (2013.01); *A61M 3/0202* (2021.05); *B06B 1/0284* (2013.01); (Continued)

(58) Field of Classification Search
CPC ... A61B 2217/005; A61B 2017/00199; A61M 3/0202; A61M 2205/581; A61M 3/0275; (Continued)

(56) References Cited

U.S. PATENT DOCUMENTS 4,826,482 A * 5/1989 Kamen ...................... G01F 1/34
                                                    604/246
5,279,547 A * 1/1994 Costin ................. A61F 9/00745
                                                    604/22
(Continued)

FOREIGN PATENT DOCUMENTS

DE        3234621 A1    3/1984
EP        0956840 A2    11/1999
(Continued)

OTHER PUBLICATIONS

U.S. Appl. No. 17/357,587, titled, "Accurate Irrigation Rate Measurement System and Method," filed Jun. 24, 2021.
(Continued)

*Primary Examiner* — Peter J Macchiarolo
*Assistant Examiner* — Anna Josephine Saunders

(57) ABSTRACT

A system includes an enclosure, an irrigation retainer, one or more sensors, and a processor. The irrigation retainer is coupled with the enclosure and configured to accept an irrigation container holding irrigation fluid for pumping to a phacoemulsification handpiece. The one or more sensors are coupled with the irrigation retainer and configured to provide at least one signal indicative of a remaining amount of the irrigation fluid. The processor is configured to receive the at least one signal, and in response to the at least one signal, output an estimation of the remaining amount of the irrigation fluid in the irrigation container or an estimation of the amount of irrigation fluid used.

17 Claims, 4 Drawing Sheets

(51) Int. Cl.
      *B06B 1/06*          (2006.01)
      *G01R 27/02*         (2006.01)
      *G06F 3/04847*       (2022.01)
      *A61B 17/00*            (2006.01)
      *A61F 9/007*            (2006.01)

(52) U.S. Cl.
      CPC ............ *B06B 1/0614* (2013.01); *G01R 27/02*
            (2013.01); *G06F 3/04847* (2013.01); *A61B*
            *2017/00199* (2013.01); *A61B 2217/005*
            (2013.01); *A61F 9/00745* (2013.01); *A61M*
            *2205/3306* (2013.01); *A61M 2205/3393*
            (2013.01); *A61M 2205/581* (2013.01); *A61M*
            *2205/587* (2013.01); *B06B 2201/76* (2013.01)

(58) Field of Classification Search
      CPC .. A61M 2205/3306; A61M 2205/3393; A61M
            2205/587; B06B 2201/76; B06B 1/0284;
            B06B 1/0614; G01R 27/02; G06F
            3/04847; A61F 9/00745
      USPC ....... 604/67, 65, 30; 606/4, 17; 73/149, 861,
            73/1.16; 33/262
      See application file for complete search history.

(56)                  References Cited

U.S. PATENT DOCUMENTS

| | | | | |
|---|---|---|---|---|
| 5,709,670 | A * | 1/1998 | Vancaillie | ........... A61M 3/0233 |
| | | | | 604/246 |
| 6,690,280 | B2 | 2/2004 | Citrenbaum et al. | |
| 8,523,812 | B2 | 9/2013 | Boukhny et al. | |
| 8,597,228 | B2 * | 12/2013 | Pyles | .................. A61M 3/0202 |
| | | | | 604/28 |
| 9,522,221 | B2 * | 12/2016 | Muri | ....................... A61M 1/77 |
| 9,545,335 | B2 * | 1/2017 | Boukhny | .............. G16H 40/63 |
| 10,453,571 | B2 * | 10/2019 | Teodorescu | ............ A61B 34/25 |

| | | | | |
|---|---|---|---|---|
| 10,463,780 | B2 * | 11/2019 | Mallough | ............... A61M 1/72 |
| 10,596,033 | B2 * | 3/2020 | Urich | .................. A61F 9/00745 |
| 12,127,979 | B2 * | 10/2024 | Gliner | ..................... A61B 34/25 |
| 12,415,028 | B2 * | 9/2025 | Govari | ...................... B06B 3/00 |
| 2006/0079788 | A1 | 4/2006 | Anderson et al. | |
| 2006/0129140 | A1 | 6/2006 | Todd et al. | |
| 2007/0161972 | A1 | 7/2007 | Felberg et al. | |
| 2008/0147023 | A1 * | 6/2008 | Hopkins | ............. A61M 3/0201 |
| | | | | 604/319 |
| 2009/0182266 | A1 | 7/2009 | Gordon et al. | |
| 2010/0069825 | A1 | 3/2010 | Raney | |
| 2011/0112472 | A1 * | 5/2011 | Jacobson | ........... A61F 9/00736 |
| | | | | 604/67 |
| 2013/0211435 | A1 | 8/2013 | Boukhny et al. | |
| 2014/0114296 | A1 | 4/2014 | Woodley et al. | |
| 2015/0216726 | A1 | 8/2015 | Kadziauskas et al. | |
| 2016/0175543 | A1 | 6/2016 | Frankhouser et al. | |
| 2016/0220751 | A1 * | 8/2016 | Mallough | ............... A61M 1/72 |
| 2018/0028359 | A1 | 2/2018 | Gordon et al. | |
| 2018/0318131 | A1 | 11/2018 | Boukhny et al. | |
| 2021/0196515 | A1 | 7/2021 | Urich | |
| 2021/0259884 | A1 * | 8/2021 | Heeren | ................... A61M 1/77 |
| 2023/0039864 | A1 * | 2/2023 | Govari | ................. B06B 1/0284 |

FOREIGN PATENT DOCUMENTS

| | | |
|---|---|---|
| EP | 1935383 A1 | 6/2008 |
| WO | 9211814 A1 | 7/1992 |
| WO | 2008016870 A2 | 2/2008 |
| WO | 2010014937 A1 | 2/2010 |
| WO | 2016122790 A1 | 8/2016 |
| WO | 2021119616 A1 | 6/2021 |

OTHER PUBLICATIONS

U.S. Appl. No. 16/727,100, titled "Phacoemulsification Apparatus," filed Dec. 26, 2019.

* cited by examiner

INSERT PHACOEMULSIFICATION TIP INTO LENS
CAPSULE OF AN EYE ~302

ACTIVATE ASPIRATION AND IRRIGATION, AND
VIBRATION OF NEEDLE ~304

ESTIMATE REMAINING AMOUNT OF IRRIGATION
FLUID ~306

INDICATE  REMAINING AMOUNT OF IRRIGATION
FLUID TO PHYSICIAN ~308

PHACOEMULSIFICATION IRRIGATION APPARATUS WITH LOAD CELL AND OPTICAL SENSOR

CROSS-REFERENCE TO RELATED APPLICATION

This application claims the benefit of U.S. Provisional Patent Application 63/230,741, filed Aug. 7, 2021, whose disclosure is incorporated herein by reference.

FIELD OF THE DISCLOSURE

The present disclosure relates generally to phacoemulsi-fication systems, and particularly to irrigation apparatuses of phacoemulsification systems.

BACKGROUND OF THE DISCLOSURE

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cata-ract surgery. In the procedure, the surgeon makes a small incision in the sclera or cornea of the eye. Then a portion of the anterior surface of the lens capsule is removed to gain access to the cataract. The surgeon then uses a phacoemul-sification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

The present disclosure will be more fully understood from the following detailed description of the examples thereof, taken together with the drawings in which:

DETAILED DESCRIPTION OF EXAMPLES

Overview

A phacoemulsification system is used to remove a natural eye lens with a cataract by breaking the lens into smaller pieces and emulsifying them using a handpiece of the system. The eye lens fragments are then aspirated under vacuum from the eye. During the aspiration the eye is irrigated so as to maintain pressure within the eye.

Examples of the present disclosure that are described herein provide retainers, which are configured to receive a container containing irrigation fluid that is used to irrigate the eye. The retainer may be incorporated into a console that drives a handpiece of the system. Optionally the console is a desktop unit.

In various examples, the retainer comprises various sen-sors configured to provide signals indicative of the remain-ing amount of the irrigation fluid in the container. The sensors may comprise, for example, one or more load cells, for example one or more strain gauges, configured to mea-sure the weight of the irrigation fluid in the container, and/or optical sensors Examples of indications include a visual (e.g., LED illuminated) level bar, audio notification/indication and/or visual notifications/indications, such as, but limited to a sound, a blinking color, and/or a verbal notification. Another example is a haptic indication, e.g., a vibration of, for example, an element in the handpiece handle or foot pedal. Such a haptic indication may be used to alert the physician that a minimal amount of irrigation fluid is left in the container.

System Description

Figure 1:
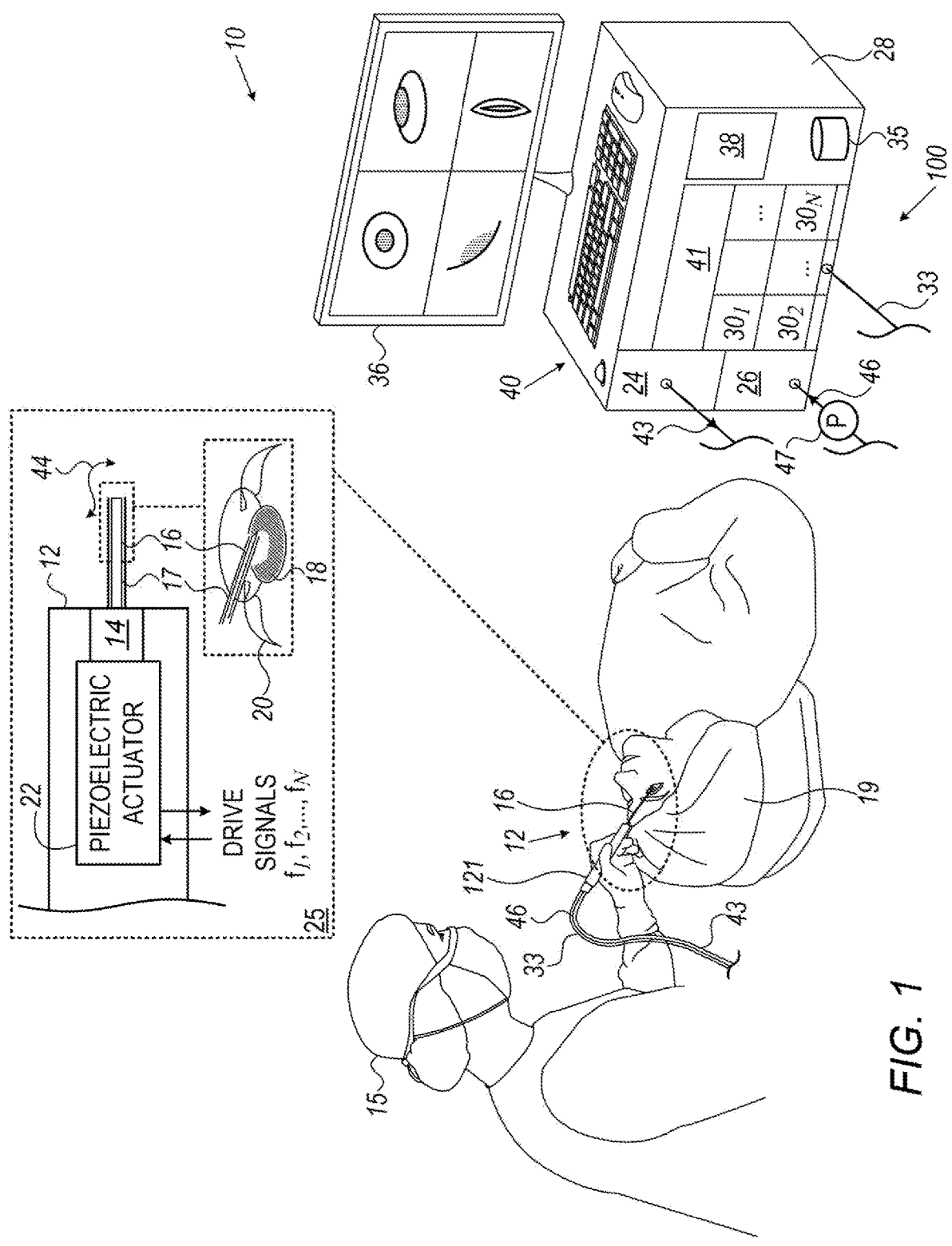
FIG. 1 is a pictorial view of a phacoemulsification system constructed to operate in accordance with an example of the present disclosure.

FIG. 1 is a pictorial view of a phacoemulsification system 10 constructed to operate in accordance with an example of the present disclosure. FIG. 1 includes an inset 25, and, as shown in the figure and the inset system 10, includes a phacoemulsification probe/handpiece 12 comprising a needle 16. Needle 16 is configured to be inserted into a lens capsule 18 of an eye 20 of a patient 19. Needle 16 is mounted on a horn 14 of probe 12, and is shown in inset 25 as a straight needle. However, any suitable needle may be used with phacoemulsification probe 12, for example, a curved or bent tip needle commercially available from Johnson & Johnson Surgical Vision, Irvine, CA, USA. A physician 15 holds handpiece 12 by a handle 121 to perform a phacoemulsification procedure on the eye 20 of patient 19. The physician may activate the handpiece using a foot pedal (not illustrated in FIG. 1).

Handpiece 12 comprises a piezoelectric actuator 22, which is configured to vibrate horn 14 and needle 16 in one or more resonant vibration modes of the combined horn and needle element. During the phacoemulsification procedure, the vibration of needle 16 is used to break a cataract into small pieces.

During the phacoemulsification procedure, an irrigation sub-system 24, which may be located in a console 28, pumps irrigation fluid from an irrigation reservoir to an irrigation sleeve 17 surrounding at least a portion of needle 16, so as to irrigate the eye 20. The combined structure of needle 16 and irrigation sleeve 17 is called hereinafter a "phacoemul-sification tip." The fluid is pumped via a tubing line (irri-gation line) 43 running from the console 28 to the probe 12. Irrigation sub-system 24 is described in more detail below.

An aspiration sub-system 26, also typically located in console 28, aspirates eye fluid and waste matter (e.g., emulsified parts of the cataract) from the patient's eye 20 via needle 16 to a collection receptacle (not shown). Aspiration sub-system 26 comprises a pump which produces a vacuum that is connected from the sub-system to probe 12 by an aspiration tubing line 46. A gauge or sensor 47 in line 46 measures the aspiration vacuum and/or pressure. Gauge 47 may be in any convenient location in line 46, including, but not limited to, a location in or in proximity to handpiece 12 or a location in or in proximity to the console.

Irrigation sub-system 24 and aspiration sub-system 26 are both controlled by a processor 38. The processor controls the flow volume rate at which the irrigation sub-system pumps fluid. The processor also controls the vacuum, pressure, and/or aspiration rate of the aspiration sub-system, using a pressure reading from gauge 47.

Some or all of the functions of processor 38 may be combined in a single physical component or, alternatively, implemented using multiple physical components. The physical components may comprise hard-wired or programmable devices, or a combination of the two. In some examples, at least some of the functions of processor 38 may be carried out by suitable software stored in a memory 35. The software may be downloaded to a device in electronic form, over a network, for example. Alternatively, or additionally, the software may be stored in tangible, non-transitory computer-readable storage media, such as optical, magnetic, or electronic memory.

Processor 38 may receive user-based commands via a user interface 40, which may include setting and/or adjusting a vibration mode, power level, duty cycle, and/or a frequency of piezoelectric actuator 22, setting and/or adjusting a stroke amplitude of needle 16, and setting and/or adjusting an irrigation rate, an aspiration rate, and/or an aspiration vacuum of irrigation sub-system 24 and aspiration sub-system 26. Additionally, or alternatively, processor 38 may receive user-based commands from controls located in handpiece 12, to, for example, select a trajectory 44, or another trajectory, for needle 16. The implementation of a trajectory, such as trajectory 44, is further described below.

Processor 38 may present results of the phacoemulsification procedure on a display 36. In an example, user interface 40 and display 36 may be one and the same, such as a touch screen graphical user interface.

The system illustrated in FIG. 1 may include further elements, which are omitted for clarity of presentation. For example, physician 15 typically performs the procedure using a stereo-microscope or magnifying glasses, neither of which are shown. Physician 15 may use other surgical tools, in addition to probe 12, which are also not shown to maintain clarity and simplicity.

Console 28 further comprises a multi-channel piezoelectric drive system 100 comprising drive modules $30_1$, $30_2$, . . . $30_N$, each coupled, using wiring in a cable 33, to a stack of piezoelectric crystals of piezoelectric actuator 22. Drive modules $30_1$, $30_2$, . . . $30_N$, generically termed drive modules 30, are controlled by processor 38 and convey phase-controlled driving signals via cable 33 to piezoelectric actuator 22. In response, piezoelectric actuator 22 vibrates needle 16, which performs a vibrational/ultrasound trajectory 44, the trajectory typically comprising one, or a combination of, longitudinal, transverse, and/or torsional ultrasonic vibrations synchronized one with the other. System 100 is described further below, with reference to FIG. 2.

Irrigation System with Load Cell and Optical Sensor

Figure 2A:
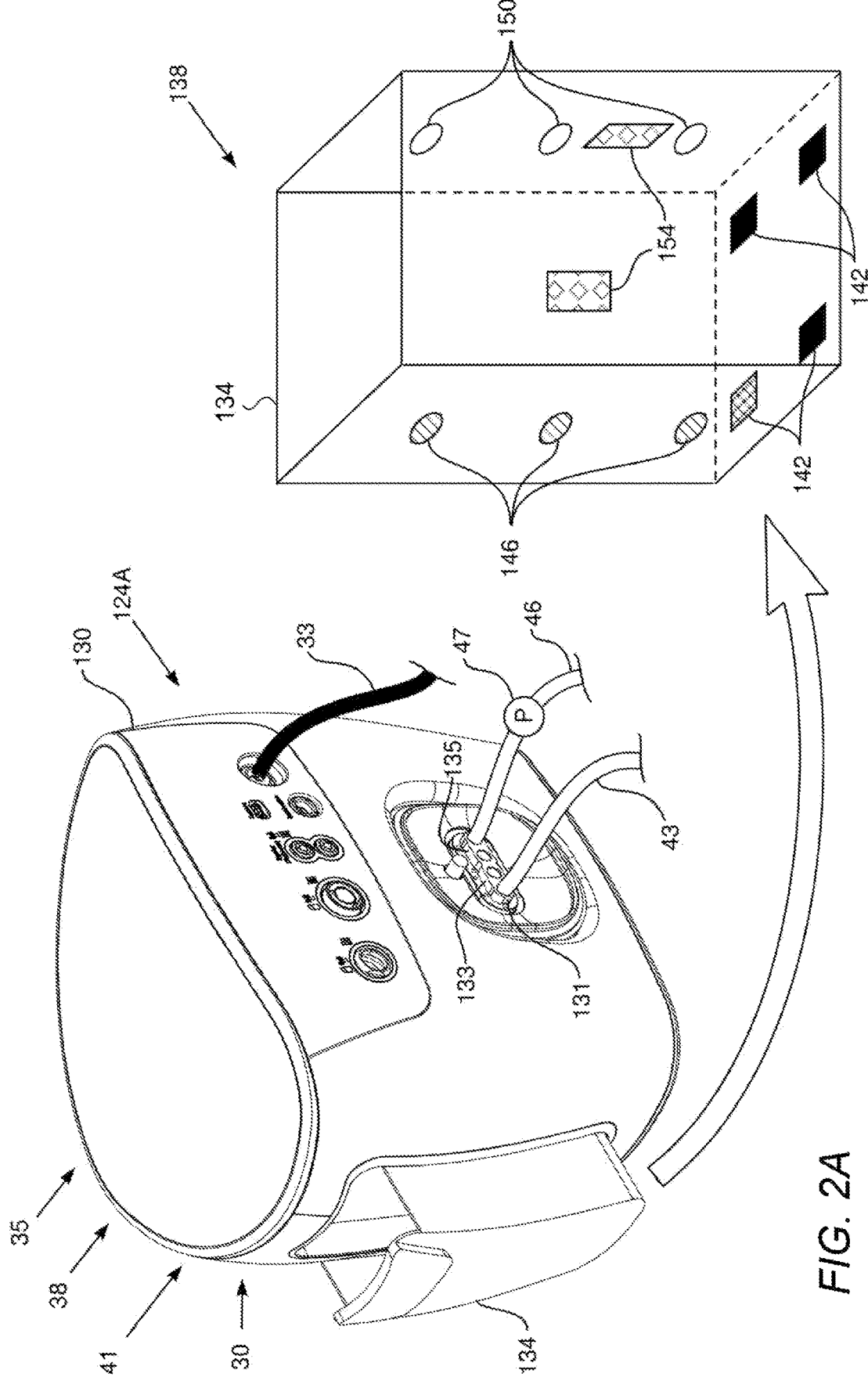
FIGS. 2A, 2B and 2C are schematic, pictorial illustrations of consoles that may be used in the phacoemulsification system of FIG. 1, in accordance with examples of the present disclosure.
Figures 2B, 2C:
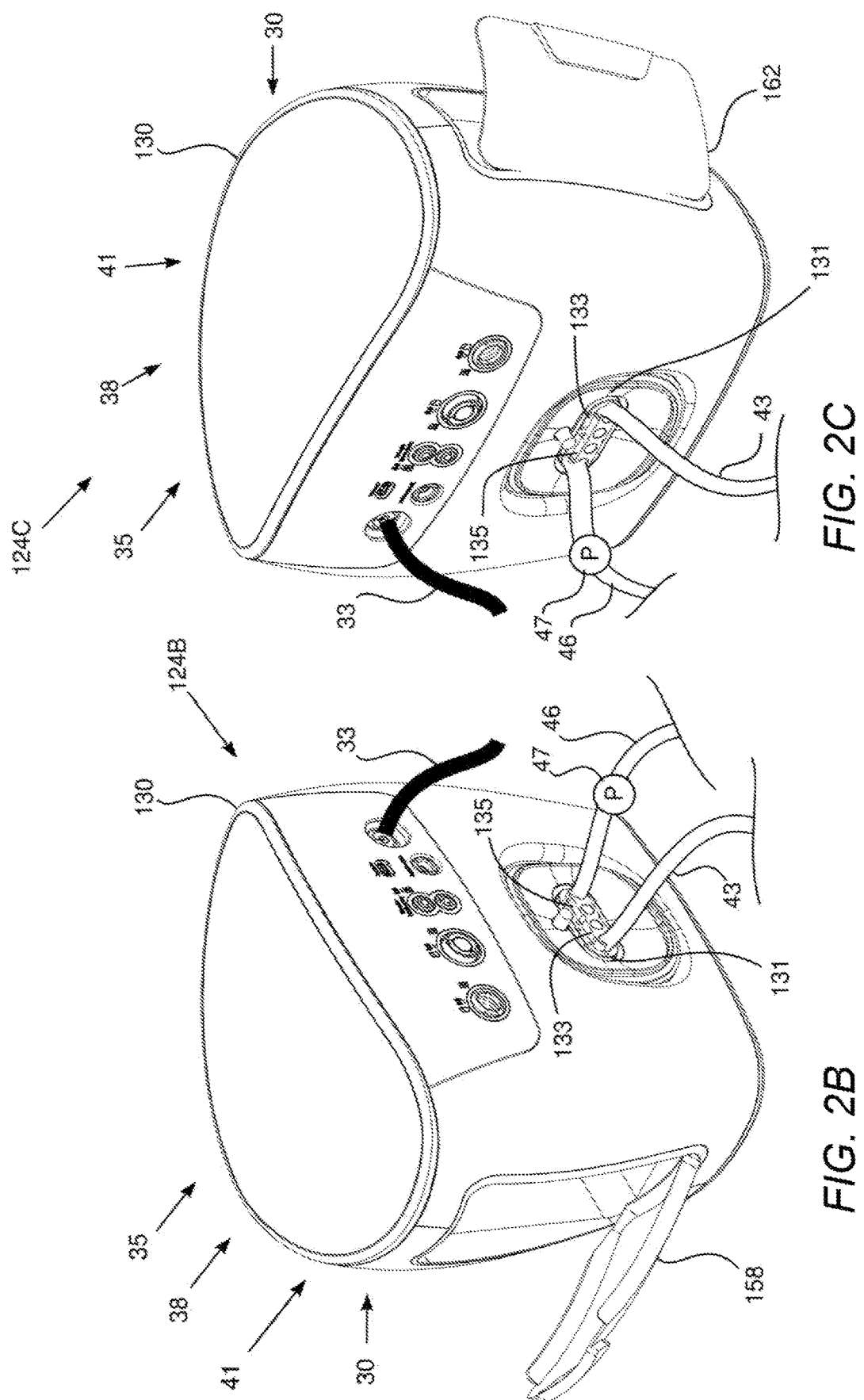

FIGS. 2A, 2B, and 2C are schematic, pictorial illustrations of consoles 124A, 124B, and 124C that may be used in apparatus 10, in accordance with examples of the present disclosure. Consoles 124A, 124B, and 124C are standalone systems, typically constructed to be placed on a flat surface such as a desk. Any of consoles 124A, 124B, and 124C may be used in place of console 28, as is described below.

Referring to FIG. 2A, console 124A comprises an enclosure 130 which is configured to accept an irrigation/aspiration cartridge 131 that is typically constructed as a disposable unit, but may be a reusable unit. Cartridge 131 comprises a progressive cavity irrigation pump 133 that is connected to irrigation tubing line 43 at its outlet. Cartridge 131 also comprises a progressive cavity aspiration pump 135 that is connected to aspiration line 46 at its inlet, the line having gauge 47 located therein. Processor 38 is located within enclosure 130.

Also within the enclosure, not shown in the drawing, are motors for driving pumps 133 and 135. The motors are controlled by processor 38. An irrigation/aspiration cartridge similar to cartridge 131 is described in U.S. patent application Ser. No. 17/318,665, filed May 12, 2021, titled "Disposable Pump Cartridge," which is assigned to the assignee of the present patent application.

It will be understood that irrigation pump 133 and aspiration pump 135, with their driving motors, respectively operate substantially as irrigation sub-system 24 and aspiration sub-system 26 of system 100, described above with reference to FIG. 1.

Additionally located within the enclosure 130 are memory 35, driving modules 30, and switching circuitry 41. Signals from modules 30 and circuitry 41 are transferred via cable 33 to piezoelectric actuator 22 of handpiece 12.

An irrigation retainer 134 in enclosure 130 is configured to receive an irrigation container (not seen in the figures), which typically comprises a bag or a bottle filled with irrigation fluid, e.g., balanced salt solution, and which, when placed within irrigation retainer 134, is connected internally to the inlet of irrigation pump 133. In the example of FIG. 2A, irrigation retainer 134 comprises a drawer that is configured to slide out from the enclosure 130 so as to receive the irrigation container, and then to slide back into the enclosure with the container.

As illustrated in a schematic callout 138, retainer 134 comprises in its base one or more load cells, in the present example a plurality of substantially similar load cells 142. In a disclosed example, load cells 142 comprise strain gauges, but other types of load cells, such as, but not limited to, piezoelectric load cells, may be used as load cells 142. Also, in an example as illustrated in the callout, irrigation retainer 134 comprises, on one side of the retainer, one or more optical emitters 146, typically configured to emit light in the visible spectrum. On an opposite side of the retainer there are one or more optical sensors 150, which provide signals in response to light received from emitters 146. In an example, irrigation retainer 134 may also comprise one or more shock absorbers 154, assumed by way of example to be positioned on the sides of the irrigation retainer, but other positions are possible and envisioned.

At the beginning of a procedure retainer 134 is slid out from the enclosure 130, and an irrigation container, filled with irrigation fluid, e.g., balanced salt solution, is placed within the irrigation retainer 134 and connected to the inlet of the irrigation pump 133. The irrigation retainer 134 is then slid back into the enclosure 130.

Processor 38 then activates load cells 142, emitters 146, and sensors 150. During the procedure, shock absorbers 154 dampen any motion of the fluid in the container. From signals generated by the load cells 142, the processor estimates a weight of irrigation fluid present in the irrigation container. In addition, from signals received from sensors 150, the processor estimates a level of fluid present in the container. From one or both estimates, the processor is able to provide an indication to physician 15 of the amount of irrigation fluid, i.e., a weight or a level, in the irrigation container and/or the amount of irrigation fluid used. The indication may be provided graphically on display 36, or by any other convenient means.

Apart from the differences described below, the operation of consoles 124B and 124C (FIGS. 2B, 2C) is generally similar to that of console 124A (FIG. 2A), and elements indicated by the same reference numerals in all sub-systems are generally similar in construction and in operation.

In console 124B (FIG. 2B), an irrigation retainer 158 serves the same function as irrigation retainer 134 of console 124A. As illustrated in FIG. 2B, irrigation retainer 158 comprises a door that opens downwards, using a horizontal hinge, to receive an irrigation container, and is then closed up to locate the container in enclosure 130. In another example, the horizontal hinge may be located at the top such that the door may open upwards and be closed by pushing downwards. In console 124C (FIG. 2C), an irrigation retainer 162 serves the same function as irrigation retainer 134 of console 124A. As illustrated in FIG. 2C, retainer 162 comprises a door which opens sideways, using a vertical hinge, to enable insertion of an irrigation container into enclosure 130, and then is closed when the container is in enclosure 130. In an example, the door may open from the left or the right.

Consoles 124B and 124C both comprise load cells 142, emitters 146, sensors 150, and optional shock absorbers 154, generally as described for console 124A.

Referring back to FIG. 1, irrigation sub-system 24 also comprises load cells 142, emitters 146, sensors 150, and optional shock absorbers 154. These elements are used by processor 38, substantially as described above for console 124A, to provide an indication to physician 15 of the amount of irrigation fluid remaining in the irrigation container.

It will be understood that the locations of load cells 142, emitters 146, sensors 150, and optional shock absorbers 154 in consoles 124B and 124C may be different from the locations described above for console 124A. One having ordinary skill in the art is able to determine such locations without undue experimentation, mutatis mutandis, and all such locations are assumed to be comprised within the scope of the present disclosure. Further alternatively, the retainer may comprise only load cells and no optical emitter/sensors, or only optical emitter/sensors and no load cells. In addition, in any example configuration, the irrigation retainer 134 may also have one or more shock absorbers 154. Moreover, in other examples, the aspiration pump is located externally to the enclosure 130.

Figure 3:
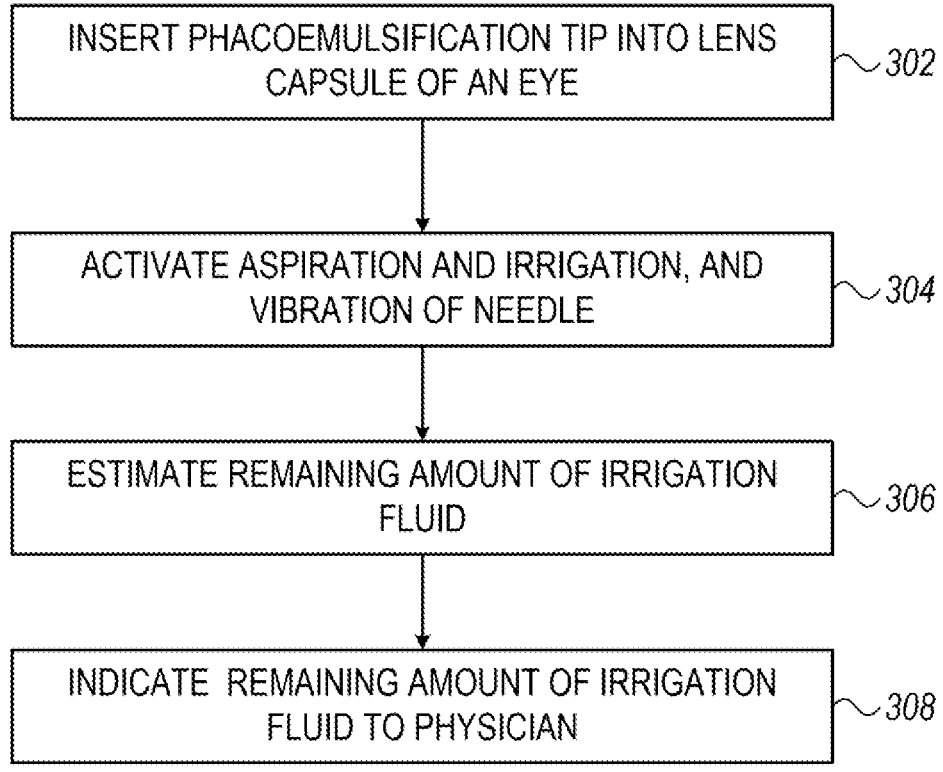
FIG. 3 is a flow chart describing steps providing a physician with an estimated quantity of irrigation fluid remaining in a container included in consoles of FIGS. 2A, 2B, and 2C, in accordance with an example of the present disclosure.

FIG. 3 is a flow chart describing steps providing a physician with an estimation of the amount of irrigation fluid remaining in a container included in consoles of FIGS. 2A, 2B, and 2C, in accordance with an example of the present disclosure.

The process begins with physician 15 inserting the phacoemulsification tip of probe 12 into a lens capsule 18 of an eye 20, at a phacoemulsification needle insertion step 302.

At a phacoemulsification step 304, physician 15 presses a foot pedal to a first position to activate irrigation and subsequently to a second position to activate aspiration, and finally, when the foot pedal is pressed and placed in a third position, the needle 16 is vibrated to perform the phacoemulsification.

During phacoemulsification, processor 41 estimates the 30 remaining amount of the irrigation fluid in the container included in one of consoles 124A, 124B, and 124C, at an irrigation fluid level estimation step 306. The processor 10 estimates the remaining amount using at least one of a) the load cells, and (b) the optical emitter/sensor setup. The load cell gives a weight of the remaining fluid, whereas the optical signal gives a height of the remaining fluid in the container. The first method can be used with a bag or bottle (e.g., when the weight of the container without fluid is known), while the second method assumes a known geometry of the container and may not be suitable for a bag.

The methods do not require knowledge of an initial volume. Rather, a reoccurring measurement of a remaining amount provides up to date information. However, if the physician needs to know how much irrigation was used, he may instruct the processor to do so. The processor then saves the initial amount, and any increased amount (e.g., when replacing a bag or refilling the container), and subtracts the actual amount remaining from the initial amounts to indicate the user how much irrigation fluid was consumed. Finally, the processor indicates to physician 15 the remaining amount of irrigation fluid in the container, for example, graphically (e.g., in a form of level bar) on display 36. As another example the processor outputs (via a loudspeaker) verbal notification of the remaining amount.

The example flow chart shown in FIG. 3 is chosen purely for the sake of conceptual clarity. For example, additional steps, such as providing an audiovisual alert of a minimal level of irrigation fluid reached, are omitted for simplicity and clarity of presentation.

EXAMPLES

Example 1

A system (124A, 124B, 124C) includes an enclosure (130), an irrigation retainer (134, 158, 162), one or more sensors, and a processor (38). The irrigation retainer is coupled with the enclosure and configured to accept an irrigation container holding irrigation fluid for pumping to a phacoemulsification handpiece (12). The one or more sensors are coupled with the irrigation retainer and configured to provide at least one signal indicative of a remaining amount of the irrigation fluid. The processor is configured to receive the at least one signal, and in response to the at least one signal, output an estimation of the remaining amount of the irrigation fluid in the irrigation container.

Example 2

The system (124A, 124B, 124C) according to example 1, wherein the one or more sensors comprise one or more strain gauges configured to sense a weight of the irrigation fluid in the container.

Example 3

The system (124A, 124B, 124C) according to example 1, wherein the one or more sensors comprise one or more piezoelectric load sensors configured to sense a weight of the irrigation fluid in the container.

Example 4

The system (124A, 124B, 124C) according to claim 1, wherein the one or more sensors comprise one or more optical emitters and one or more optical sensors (150) configured to sense a level of the irrigation fluid in the container.

Example 5

The system (124A, 124B, 124C) according to any of examples 1 through 4, wherein the processor (38) is configured to estimate at least one of a weight of the irrigation fluid and a level of the irrigation fluid in the container, and, in response to the estimation, determine the remaining amount of irrigation fluid.

Example 6

The system (124A, 124B, 124C) according to any of examples 1 through 5, wherein the processor (38) is configured to output an estimate of an amount of the irrigation fluid already used.

Example 7

The system (124A, 124B, 124C) according to any of examples 1 through 6, wherein the processor (38) is configured to output the estimation by at least one of an audio or a visual indicator.

Example 8

The system (124A, 124B, 124C) according to any of examples 1 through 7, wherein the audio indicator comprises a sound or verbal notification of the amount estimated as remaining.

Example 9

The system (124A, 124B, 124C) according to any of examples 1 through 7, wherein the visual indicator comprises a LED illuminated level bar.

Example 10

A method includes coupling an irrigation container holding irrigation fluid with an irrigation retainer (134, 158, 162) of an enclosure (130) of a system (124A, 124B, 124C) for pumping the irrigation fluid to a phacoemulsification handpiece (12). The irrigation retainer has one or more sensors and the one or more sensors are configured to provide at least one signal indicative of an amount of irrigation fluid remaining in the irrigation container. Received in a processor (38) is the at least one signal, and in response to the at least one signal, an estimation is outputted of the amount of irrigation fluid remaining in the irrigation container or an estimation of an amount of the irrigation fluid used.

Although the examples described herein mainly address phacoemulsification, the methods and systems described herein can also be used in other surgical applications that may require irrigation.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

8

The invention claimed is:

1. A system, comprising:
an enclosure;
an irrigation retainer coupled with the enclosure and configured to accept, within the irrigation retainer, an irrigation container holding irrigation fluid for pumping to a phacoemulsification handpiece;
one or more sensors coupled with the irrigation retainer and configured to provide at least one signal indicative of a remaining amount of the irrigation fluid; and
a processor, configured to receive the at least one signal, and in response to the at least one signal, output an estimation of the remaining amount of the irrigation fluid in the irrigation container.

2. The system according to claim 1, wherein the one or more sensors comprise one or more strain gauges configured to sense a weight of the irrigation fluid in the container.

3. The system according to claim 1, wherein the one or more sensors comprise one or more piezoelectric load sensors configured to sense a weight of the irrigation fluid in the container.

4. The system according to claim 1, wherein the one or more sensors comprise one or more optical emitters and one or more optical sensors configured to sense a level of the irrigation fluid in the container.

5. The system according to claim 1, wherein the processor is configured to estimate at least one of a weight of the irrigation fluid and a level of the irrigation fluid in the container, and, in response to the estimation, determine the remaining amount of irrigation fluid.

6. The system according to claim 1, wherein the processor is configured to output an estimate of an amount of the irrigation fluid already used.

7. The system according to claim 1, wherein the processor is configured to output the estimation by at least one of an audio or a visual indicator.

8. The system according to claim 7, wherein the audio indicator comprises a sound or verbal notification of the amount estimated as remaining.

9. The system according to claim 7, wherein the visual indicator comprises a LED illuminated level bar.

10. A method, comprising:
coupling an irrigation container holding an irrigation fluid with an irrigation retainer of an enclosure of a system,
wherein the irrigation retainer is configured to accept, within the irrigation retainer, the irrigation container for pumping the irrigation fluid to a phacoemulsification handpiece;
wherein the irrigation retainer comprises one or more sensors and the one or more sensors are configured to provide at least one signal indicative of an amount of irrigation fluid remaining in the irrigation container; and
in a processor, receiving the at least one signal, and
in response to the at least one signal, outputting an estimation of the amount of irrigation fluid remaining in the irrigation container or an estimation of an amount of the irrigation fluid used.

11. The method according to claim 10, wherein the one or more sensors comprise one or more strain gauges configured to sense a weight of the irrigation fluid in the irrigation container.

12. The method according to claim 10, wherein the one or more sensors comprise one or more piezoelectric load sensors configured to sense a weight of the irrigation fluid in the irrigation container.

13. The method according to claim 10, wherein the one or more sensors comprise one or more optical emitters and one or more optical sensors configured to sense a level of the irrigation fluid in the irrigation container.

14. The method according to claim 10, further comprising estimating at least one of a weight of the irrigation fluid and a level of the irrigation fluid in the irrigation container, and, in response to the estimation, determining the remaining amount of irrigation fluid.

15. The method according to claim 10, wherein outputting the estimation comprises outputting by at least one of an audio or a visual indicator.

16. The method according to claim 15, wherein outputting by the audio indicator comprises a sound or verbal notification of the amount estimated to be remaining in the irrigation container or the estimated amount of the irrigation fluid used.

17. The method according to claim 15, wherein outputting by the visual indicator comprises a LED illuminated level bar of the amount estimated to be remaining in the irrigation container or the estimated amount of the irrigation fluid used.

\* \* \* \* \*